United States Patent [19]

Brugging et al.

[11] Patent Number: 5,585,536
[45] Date of Patent: ***Dec. 17, 1996

[54] PREGERMINATED SEEDS

[75] Inventors: Gerhard T. Bruggink; Peter Van der Toorn, both of Enkhuizen, Netherlands

[73] Assignee: Sandoz Ltd., Basel, Switzerland

[*] Notice: The term of this patent shall not extend beyond the expiration date of Pat. No. 5,522,907.

[21] Appl. No.: 387,759

[22] PCT Filed: Aug. 31, 1993

[86] PCT No.: PCT/EP93/02353

§ 371 Date: Feb. 15, 1995

§ 102(e) Date: Feb. 15, 1995

[87] PCT Pub. No.: WO94/05145

PCT Pub. Date: Mar. 17, 1994

[30] Foreign Application Priority Data

Sep. 1, 1992 [GB] United Kingdom ............... 9218513

Dec. 4, 1992 [GB] United Kingdom ............... 9225392

[51] Int. Cl.$^6$ ............... A01H 5/00; A01C 1/00
[52] U.S. Cl. ............... 800/200; 47/57.6; 47/58; 47/DIG. 9
[58] Field of Search ............... 47/57.6, 58, DIG. 9; 800/200

[56] References Cited

FOREIGN PATENT DOCUMENTS 0202879  5/1986  European Pat. Off. .

*Primary Examiner*—David T. Fox
*Assistant Examiner*—Elizabeth F. McElwain
*Attorney, Agent, or Firm*—Lynn Marcus-Wyner

[57] ABSTRACT

Pregerminated seeds comprising desiccation tolerant emerged radicles, processes for their production, and plants produced from such seeds.

17 Claims, No Drawings

PREGERMINATED SEEDS

The present invention relates to pregerminated seeds having desiccation tolerant emerged radicles, a process for obtaining such seeds and plants derived therefrom.

BACKGROUND OF THE INVENTION

Several attempts have been made to produce pregerminated seeds which give rise to consistently high and reproducible rates of germination in the field for many species of plants. However, such attempts have proven to be unsatisfactory since inter alia the storage life of such seeds is generally of limited duration or requires the employment of specialised storage facilities. Furthermore, pregerminated seed has not hitherto been considered amenable for sowing with conventional sowing methods and equipment i.a.because of the problem of seed dehydration under sowing conditions.

Granted patent specification EP 202879 B1, describes the obtention of high viability seed lots which are selected on the basis of having emerged radicles which have a moisture content at which radicle development is suspended without loss of seed viability. There is no suggestion that induction of desiccation tolerance in the radicle is advantageous and can lead to a product comprising germinated seeds which are capable of being stored at ambient temperatures for long periods of time without the need for specialised storage conditions. The high viability seed lots obtainable according to the disclosure of EP 202 879 B1 are not desiccation tolerant as indicated by several statements in said specification and as supported by the examples hereinafter demonstrating essential differences between the desiccation tolerant pregerminated seeds obtainable according to the teaching of this invention and the pregerminated seeds obtainable according to the conditions disclosed in EP 202 879 B1.

Many reports have appeared in the scientific literature of the effect upon seeds or seedlings of desiccation stress. One such report states that desiccation tolerance may be due to the presence of disaccharides such as sucrose and/or the presence of other plant sugars such as oligosaccharides. However, such a desiccation tolerance in the seed has been observed to be lost upon the emergence of the radicle from the seed coat and it is at this critical stage of germination that the ability to induce desiccation tolerance in the radicle has not hitherto been considered practicable [Koster K. L. and Leopold A. C. Plant Physiol. 88:829–832 (1988)].

Other workers have reported that maturing *Barssica campestris* seed acquire desiccation tolerance during seed development and that this has been observed to be concomitant with elevated levels of sucrose content. However, attempts at inducing desiccation tolerance in the emerged radicle of germinated seeds was neither described nor suggested [Leprince O. et al, Plant, Cell, and Environment 13:539–546 (1990)].

The art generally teaches of the loss of desiccation tolerance in germinated seeds. It has now surprisingly been found that desiccation tolerance can be induced in seeds having an emerged radicle. Furthermore, it has now been found that seeds comprising desiccation tolerant emerged radicles are capable of being sown without the need for employing refinements to sowing methods such as the application of encapsulating gels to pregerminated seed and the like. Surprisingly, seeds comprising desiccation tolerant emerged radicles as herein described are capable of being sown using conventional non-germinated seed sowing methods and equipment without substantial deleterious effect on seed viability.

Advantages of sowing seed in which the radicle has emerged include faster germination times once sown and provided that the seed supplier can guarantee a high seed viability per batch of seeds sown, a more reliable estimate of how much seed is required for sowing and hence more efficient growing methods.

One benefit of inducing desiccation tolerance in the emerged radicle of pregerminated seeds is that such seeds can be dried back to a moisture content approaching that of non-germinated seed. Thus, treated seed comprising desiccation tolerant emerged radicles is capable of being stored for long periods of time at ambient temperature i.e. without the need for employing specialised storage facilities such as refrigeration facilities and the like.

A further advantage is that seed comprising desiccation tolerant emerged radicles which have not been further dried back can be sown naked i.e. using conventional seed sowing methods and equipment without the need for employing encapsulating gels and the like.

SUMMARY OF THE INVENTION

An object of the present invention is to provide germinated seed comprising desiccation tolerant emerged radicles in the form of naked or pelleted seed in commercial quantities suitable for sowing in the field.

Another object is to provide germinated seeds comprising desiccation tolerant emerged radicles which have a long shelf-life and which do not require specialised conditions for transport and/or storage.

A further object is to provide a method of treating seed wherein desiccation tolerance is imparted to at least a part of the radicle of germinated seed.

These and other objects and advantages of the present invention will become apparent from the following description.

DETAILED DESCRIPTION OF THE INVENTION

According to the present invention there are provided pregerminated seeds comprising desiccation tolerant emerged radicles.

For the purposes of the present invention the terms 'pregerminated seeds' and 'germinated seeds' are used interchangeably and are defined as seeds in which the radicle and/or hypocotyl has protruded or emerged from the seed coat or pericarp. The protruded or emerged radicle can be surrounded by endosperm (e.g. Cyclamen) or not depending on species. The length of the radicle may be of any length which distinguishes germinated seed from non-germinated seed. Preferably, the radicle can be of any length up to the maximum diameter of a seed. Thus, where a seed has an irregular shape, the length of the radicle can approximate the widest diameter of the seed. The most preferred length for seed coating, sowing and/or separation procedures is of the order of 2.5 mm or less depending on seed type. Suitable seed types include those which are capable of forming root primordia from at least an hypocotyl region; preferred seed types include those types which are not capable of developing a seminal root system. Examples of this category include all vegetable and flowering species of the types listed in the Handbook for Seedling Evaluation, J.Bekendam and R. Grob ISTA, Zurich, Switzerland 1979 on pages 28–29, and especially those types exemplified on pages 122–126. Seed types capable of forming roots from an hypocotyl region are also included within the ambit of the invention. Examples of seed types on pages 122–126 of the above reference which may not be considered to form a typical seminal root system but which nevertheless can be said to be capable of forming roots from a hypocotyl region include such seed types as Cyclamen and Impatiens. Preferred seed types of the invention include those of species representing the groups comprising Alliums, Antirrhinums, Begonias, Brassicaceae, Capsicums, Betas, Lycopersicons, Cucurbitaceae, Cyclamens, Dianthuses, Gazanias, Gerberas, Impatiens, Lobelias, Nicotianas, Pelargoniums, Petunias, Phloxes, Primulas, Raphanuses, Salvias, Solanaceae, Tagetes, Verbenas, Vincas, Violas, Apiums, Daucuses, Chicoriums, and Zinnias. Most preferred seed types include those of species represented by the groups Brassicaceae, Capsicums, Impatiens, Cyclamens, Petunias, Lycopersicons and Violas. Also encompassed within the ambit of the present invention are plants grown from seed as herein described.

The germinated seeds comprising desiccation tolerant emerged radicles are more versatile than conventional germinated seed because they are able to withstand desiccation stresses imposed by the ambient environment which may arise during transport, or on sowing equipment and the like. Thus, seeds of the invention can also be subjected to further desiccation treatments which can render them storable for longer storage periods under conventional seed storage conditions relative to seeds comprising emerged radicles which have not been subjected to a desiccation tolerance induction treatment. Conventional seed storage conditions may comprise a relative humidity of from about 30% to 50% and a temperature of from about 15° C. to 20° C. Seed storage conditions may also include temperatures within the range of from about −20° C. to about 25° C. (i.e. room temperature). Alternatively, germinated seeds of the invention may be sown using conventional sowing methods and equipment without the need for special treatments such as gel encapsulation for minimising water loss and the like since the seeds can withstand further desiccation while in situ on seed sowing equipment, in open sacks and the like.

In another embodiment of the invention there are provided seeds comprising desiccation tolerant emerged radicles which are capable of being sown using conventional sowing equipment.

Typically, germinated seeds of the invention are found to have substantially elevated levels of the disaccharide sugar, sucrose in their radicles, relative to the radicles of germinated seeds which have not been subjected to a desiccation tolerance treatment as herein described. Naturally, the skilled artisan will appreciate that a pregerminated seed in which desiccation tolerance has been induced in the radicle will also have been rendered desiccation tolerant in other structures of the seed, such as for example, in cotyledon structures and the like.

'Desiccation tolerant' means that the seed radicles in which desiccation tolerance has been induced are capable of withstanding further desiccation treatments which reduce the overall moisture content of the seed to a moisture content typical for that of non-germinated seeds of the relevant species without substantially affecting the seeds ability to resume growth under favourable growing conditions, even after storage for 1,2 or more weeks. Seeds in which desiccation tolerance has been induced in the radicle can be subjected to further desiccation treatments depending on the objective.

Pregerminated seeds having desiccation tolerant emerged radicles are obtainable by maintaining pregerminated seeds during an incubation period at a moisture content sufficiently low to substantially inhibit growth of the radicle but high enough to permit other metabolic processes to continue. The optimum moisture content will depend on the particular seed type employed, and can be established by monitoring the development of metabolic processes in test samples, e.g. sucrose content increase during the incubation period. In general, the moisture content of seeds suitable for desiccation tolerance induction in the emerged radicles will lie in the range of from about 35% to 55%, more specifically of from about 35% up to about 50% by weight of the seeds. The optimum incubation conditions (incubation time, temperature, relative humidity [RH], osmotic value etc.) can likewise be established experimentally, in that for example the seeds are incubated under different conditions, then dried back to a moisture content typical for non-germinated seeds and the viability of the dried seeds then established e.g. by determining, for test samples, the percentage of seedlings obtained after storage for a certain period of time, the percentage of seeds showing root elongation or secondary root formation etc., as illustrated by the examples hereinafter. In general, the incubation temperature will lie in the range of 0° to 25° C., more preferably of 0° to 15° C. The incubation period will depend on the other incubation conditions and the particular seed type. In general, satisfactory results are obtained with an incubation period in the range of from 1 day to 10 days. Seeds comprising desiccation tolerant emerged radicles which have undergone further desiccation treatments can be stored for longer storage periods under conventional seed storage conditions relative to seeds comprising emerged radicles which have not been subjected to a desiccation tolerance induction treatment. Shelf-life of seeds of the invention can thus be lengthened with further desiccation treatments which reduce the overall moisture content of the seed to from about 4% to about 12% by weight of the seed depending on species (i.e. moisture content typical for that of non-germinated seeds of the relevant species) which does not substantially affect the ability of the radicle to resume growth upon the return of favourable growing conditions. A radicle of a seed may be viewed as being desiccation tolerant if it is capable of giving rise to further radicle growth either in the form of elongation of the primary root per se or formation and/or elongation of root primordia from a point or points located on the primary root or from the hypocotyl region, after having first undergone a desiccation tolerance induction treatment. Thus, desiccation tolerance in the emerged radicle may be restricted to at least a particular part of the emerged radicle, such as the hypocotyl region.

The radicles of germinated seeds having induced desiccation tolerance have a sucrose content that is elevated relative to the sucrose content of emerged radicles in seeds of the same species which have not undergone desiccation tolerance induction. Typically, the radicles of desiccation tolerant germination seeds have a sucrose content in the range of from about 3% up to about 15% by weight of the radicle. Naturally, the actual sucrose content of the radicle will vary depending on species. The skilled artisan will appreciate that the overall sucrose content of the seed will also increase.

In a further embodiment of the invention there are provided coated germinated seeds comprising desiccation tolerant emerged radicles.

'Coated germinated seeds' conforms to the description given above for 'germinated seeds' except that the seeds are provided with an additional protective layer or in pelleted form. The pelleting material may comprise any conventional material commonly used in the art for protecting or pelleting seed. Suitable pelleting materials include clays such as sub-bentonite and bentonite, vermiculite along with additives such as perlite, pumice, metal stearates, polyethene, polystyrene, polyurethane, talcum powder, polypropene, polyvinyl chloride, starches, loams, sugars, arabic gums, organic polymers, celluloses, flours such as wood flours, quartz powders and the like. Such materials may be added to seed of the invention using conventional layering or pelleting procedures known in the art. Examples of components which may also be incorporated into the seed coat include growth regulators such as gibberellins or auxins. Typically, the content of growth regulator will be in the range of from about 0.0001% to about 1.0% by weight of the coating material.

In a further embodiment there is provided a method of inducing desiccation tolerance in emerged radicles of germinated seeds comprising subjecting germinated seed to environmental conditions conductive to the induction of desiccation tolerance in the emerged radicle.

In a further embodiment there is provided a method of obtaining germinated storable seeds comprising desiccation tolerant emerged radicles which comprises i) subjecting germinated seed to environmental conditions conducive to the induction of desiccation tolerance in the emerged radicle and ii) drying back the seed to a moisture content that is substantially that of commercially available non-germinated seeds whereby step (ii) may be initiated before the desiccation tolerance induction under the conditions of step (i) has been achieved, provided the drying step (ii) is carried out sufficiently slow to permit the seed radicles to acquire desiccation tolerance before the moisture content has reached a level where metabolic processes are substantially discontinued.

In general, the storable germinated seeds according to the invention will have a moisture content of from 4% to 12% by weight of the seeds.

The germinated seed used as starting material may be obtained in conventional manner. It will conveniently be obtained by germinating seed in an appropriate seed germinating environment. A 'seed germinating environment' is one wherein seeds may freely germinate at least to the extent that radicle protrusion occurs. The environment must be adequately moist, aerated or oxygenated, and capable of promoting seed germination to at least the stage of radicle protrusion from the seed coat or pericarp. An example of such an environment is the aerated water column wherein the degree of aeration is sufficient to keep the seeds of interest buoyed or in suspension. The amount of seed per unit volume can be any suitable amount. A suitable amount can be from 1–200 g seeds/l. In a preferment, the amount of seed does not rise above about 25 g seeds/l of water. The actual amount of seed per unit volume of water is dependent on species. Generally, the temperature of the seed germinating environment is one which permits or promotes the germination of the seed. A suitable temperature of the germinating environment can lie in the range of from 5° C. to about 30° C. depending on species. Preferably, the temperature of the germinating environment lies within the range of from about 15° C. to about 25° C.

Other conventional additions to the germinating environment may include further excipients, diluents, additives, factors and regulators as required, which may help in promoting or improving germination or of enhancing secondary root primordia induction in the emerged radicle. Such additions may include but are not limited to the use of plant growth regulators or hormones, for example a gibberellin biosynthesis inhibitor such as pactobutrazol (e.g. where it is desired to enhance survival of primary roots), a gibberellin (e.g. where it is desired to stimulate secondary root growth) or an auxin which may be added to the germination environment to a concentration of from about 0.0001% to about 1.0% by weight of seed germinating environment. Conventional additions to the germinating environment also encompasses the use of physical stimuli.

Instead of the aerated water column other environments such as moisture filter paper may be used. Once germination or radicle protrusion from the seed coat or pericarp is observed, the germinating seeds are separated from the others using conventional techniques known in the art. Typically, separation techniques rely on physical differences between germinated seed and non-germinated seed such as size, weight, shape, and the like. An important factor in seed separation is the selection of seed having radicles of the right length. The length of the radicles is preferably up to and including the length or diameter of the seed. Usually, the seeds are surface dried before the induction of desiccation tolerance, using procedures commonly employed in the art.

Desiccation tolerance can be induced in the emerged radicle by any one of several methods. During this induction phase, growth of the radicle is substantially inhibited however the moisture content of the seeds is such so as to permit other metabolic processes to continue. Such moisture content will depend on the particular seed species but will in general not be lower than about 35% by weight of the seed. Some methods rely on either with-holding water from or with-drawing water from the seed over an 'incubation' period. In principle it is sufficient to with-hold water, since the metabolic processes require water and the overall moisture content of the seeds is reduced when water is with-held. Thus, the initial moisture content may be equal to that of germinating seeds, although a somewhat lower moisture content gives a quicker induction. The aim of the incubation is to place the seed under a mild to moderate water stress.

One method of inducing desiccation tolerance in seeds involves the incubation of seeds comprising emerged radicles for long periods of time under conditions wherein moisture loss is prevented. An example is where the seeds are held in a closed container such that a minimal exchange of gases is permitted, for up to several days. For instance such a container can be a petri dish with a loose fitting lid, or a larger container having a loose fitting lid. The seeds can be incubated at any temperature within the range of from about 0° C. up to about 25° C. Preferably, seeds are incubated at suitably low temperatures such as from about 0° C. to about 15° C., for example, to minimise the risk of infestation with pathogens. The period of time and temperature required for incubation may vary from species to species and it may be measured in terms of days stretching into weeks or longer. Preferably, the incubation period may be any period of time from about 1 day up to about 10 days.

In the above case, where a seed coating formulation is to be applied to the seed, a coating may be conferred on the seed either before or after the incubation step and before or after any subsequent drying step.

In a variant of the incubation alternative outlined above, germinated seeds may first be dried back relatively quickly under conventional drying procedures and then submitted to incubation conditions. Thus, the moisture content may initially be reduced to e.g. a moisture content which is about 10% lower than that which germinated seeds normally possess. Satisfactory results are obtained when the moisture content is between about 0.5% to 5% lower, particularly between about 2% and 5% lower than that which germinated seeds normally possess depending on species. In general, it is advantageous not to reduce the moisture content to less than about 35% by weight of the seeds. For instance, the seeds can be dried back under conditions wherein the temperature lies within the range of from 0°–25° C., at a relative humidity within the range of from 30%–90%, in still air or in flowing air at speeds typical for drying back seeds. For example the airflow speed may be at any speed up to 2 m/s or faster. The period of time may be for any suitable time interval up to about 24 hrs depending on drying conditions employed. Suitable drying conditions are 20 C, at a relative humidity of 40% in air flowing at a speed of 2 m/s over 5 minutes.

Typically, seeds in which desiccation tolerance is to be induced in the radicle are dried back to an overall water content sufficient to permit metabolic processes to continue but sufficiently below that of germinating seed to substantially inhibit radicle growth, typically about 35% to about 55%, more preferably 35% to 50% by weight of the seed depending on species.

After drying back, the seeds are transferred to an environment wherein moisture loss is prevented, (e.g. a closed container), and subjected to incubation treatments as described herein before in order to induce desiccation tolerance in the radicle. As above, where a seed coating formulation is to be applied to the seed, a coating may be conferred on the seed either before or after the induction step and before or after any subsequent drying step.

Water content of seeds or emerged radicles is calculated using the following formula:

$$\frac{Wi - Wa}{Wi} \times 100$$

where
Wi=weight initial
Wa=weight after oven drying seeds or radicles at 103° C. overnight An alternative method of inducing desiccation tolerance into emerged radicles of seeds includes subjecting such seeds to a water stress via osmosis. For example, selected seeds may be transferred to an aqueous solution possessing an osmotic value of from about −0.5 to about −4.0 MPa. The actual osmotic value of the solution can vary between species, however, it should be such that growth of the radicle is inhibited but that the moisture content of the seeds is sufficiently high so as to permit other metabolic processes to continue. In this state seeds experience a mild water stress due to a lack of availability of free water. Typically, the seeds are contacted with a solution of a suitable osmoticum such as PEG 8000, mannitol, or a salt solution such as NaCl and the like. Plant growth regulators such as methyl jasmonate, and auxins e.g. indole butyric acid (IBA), can also be added to the osmoticum solution at a concentration of between about 0.0001% to about 1.0% by weight. Alternatively, seeds may be contacted with a solution of a suitable plant hormone such as abscisic acid (ABA). Preferably, the seeds are soaked in a suitable osmoticum solution in an aerated column as hereinbefore described. The actual osmoticum solution used is not critical to the invention as long as the seeds are not harmed by it. The contact time may be for a time interval measured in days extending to weeks or longer, preferably for a period of 1–10 days at a temperature lying in the range of from 0° to 25° C. More preferably, the contact time is from 3–10 days. The contact period is preferably carried out at a temperature at less than 10° C. After the contacting period the seeds are washed in water.

After inducing desiccation tolerance in the emerged radicle seeds destined for storage purposes may be dried back to moisture contents similar to those of ungerminated seed eg from about 4% to about 12% by weight depending on species. The method of drying back after induction of desiccation tolerance in the radicle is not critical provided that a sufficient degree of desiccation tolerance has been induced in the radicle and the temperature is not too low. Conveniently the temperature is not below 10 C. For example in a method of drying, seeds can be spread out in a single layer, and left standing in still air for about 24 hrs at a relative humidity of from about 40%–75% and temperature in the range of from 10°–30° C. After the end of such a drying period, seeds are found to have reached a moisture content of between 4% and 12% by weight, depending on species.

In a further variant, the induction of desiccation tolerance in emerged radicles can be attained and combined with further desiccation in one step when producing storable seed as mentioned hereinbefore, by drying back seed comprising emerged radicles very slowly to a moisture content of ungerminated seed, e.g. of from about 4% to about 12% by weight. The time period required for this can be from 2–10 days in duration at a relative humidity lying within the range of from 75% to 90% at a temperature of about 20° C. Preferably the time interval is from about 3–7 days under appropriate drying conditions. Appropriate drying conditions include those temperature conditions as hereinbefore described. Such seeds may then be subjected to further desiccation treatments depending on design.

Storable seeds are those wherein desiccation tolerance has been induced in the radicle and which possess a moisture content in the range of from about 4% to about 12% by weight. Such seeds can be stored for periods of at least 3 months in sealed containers such as drums, plastic bags, aluminium-lined bags and the like under storage conditions of the ambient environment i.e. without the need for storing in specialised refrigeration or cooling conditions, specified temperatures, certain relative humidity and the like.

There now follow examples which further illustrate the invention. It is to be understood that the examples are not to be viewed as limiting the scope of the invention in any way. The tables referred to in the examples are shown after Example 14.

EXAMPLE 1

Desiccation tolerance and sucrose content increase during incubation of germinated Impatiens seeds in PEG-8000 solution.

25 g seeds of Impatiens (cv Impulse rose, Zaadunie BV) are germinated in 2 l of aerated water at 20° C. for 4 days. 3000 germinated seeds are selected, and centrifuged at 1300 rpm for 1 minute to remove excess water. Seeds are divided into 5 portions of 600 seeds. 4 portions are incubated on blotting paper moistened with a solution of PEG-8000, commercially available from BP Chemicals, Southampton, (324 g/l, water potential −1.5 MPa, determined following the teaching of Michel B. E. [(1983) Plant Physiology 72:66–70]), in a closed container at a temperature of 8° C. for periods of 1, 2, 3 or 6 days to induce desiccation tolerance. One portion is used as a control (i.e. non-incubated). After the induction periods, seeds are rinsed in distilled water. Moisture content of the seeds is determined at the end of the incubation periods and just after rinsing at 44% by weight using the formula as herein described.

25 seeds from each portion are used for determining sucrose content at the end of the incubation periods (i.e. immediately for control seeds), using the UV methodology as outlined in "Methods of Biochemical Analysis and Food Analysis" (1986) pp 96–98, Boehringer Mannheim. 100 seeds of each portion are sown on soil and the emergence of seedlings is counted after 14 days.

After rinsing, remaining seeds are dried in still air at 40% relative humidity (RH) and 20° C., reaching a final moisture content of 5% by weight in 24 hours. Control seeds are dried in the same manner.

After drying, seeds are stored at 40% RH and 20° C. until sowing i.e. 14 days after drying of controls.

Table 1 shows that desiccation tolerance developed gradually during the incubation period, the increase in desiccation tolerance coincided with an increase in sucrose content of the seeds.

EXAMPLE 2

Desiccation tolerance and sucrose content increase in pregerminated tomato seeds.

25 g of tomato seed are germinated in 4 l aerated water at 20° C. After 4 days, 1000 seeds with a radicle length of less than the seed diameter are selected by hand. Seeds are blotted dry and placed in a closed container at 8° C. for desiccation tolerance induction periods of 0, 1, 4, and 6 days. Moisture content of a sample of 200 seeds is determined at 48% by weight. After the induction periods the seeds are placed in still air and dried at a temperature of 25° C. and relative humidity of 40%. The final moisture content of the seeds is 7% and is reached after a time interval of about 12 hours. Sucrose content of the emerged radicles is determined at the end of the induction periods, just before drying as outlined above. Sucrose content is determined on a sample of 50 seeds using the UV methodology described in example 1. After drying, seeds are stored at 40% relative humidity and 25° C. for 14 days. 100 seeds from each induction period are planted and percent emergence determined after 5 days. Results are shown below in Table 2.

EXAMPLE 3

Slow drying induces desiccation tolerance and elevated sucrose content in pregerminated Impatiens seeds.

5 g seed of Impatiens seeds are germinated in 4 l water at a temperature of 20° C. in an aerated column. After 4 days, 1000 germinated seeds having a radicle length less than that of the seed diameter are selected by hand. All seeds are centrifuged for 2 minutes at 1300 rpm to remove excess water.

Seeds are divided into two groups. Seeds of one group are dried at three different drying rates (see below). Seeds of a second group are incubated for 5 days at 8° C. in a closed container. Moisture content of the seeds is determined at 47.5% by weight. Seeds are then dried at the same three different drying rates as the first group.

After drying, seeds are stored at 40% relative humidity and 20° C. for 14 days. Sucrose content of the seeds from both groups is determined after drying as per example 1. Seeds have a final moisture content of 5.5% by weight.

100 seeds from each group are planted and % emergence determined after 7 days at 25° C.

Drying Conditions i) Fast drying

Windspeed 1 m/s at 30% relative humidity and 25° C. Seeds have a final moisture content of 5% after 6 hours.

ii) Medium drying

Seeds are placed on trays above a saturated solution of NaCl in a chamber (1 m$^3$) having a controlled environment. Windspeed 0.05 m/s. Moisture content is maintained at a relative humidity of 75% and temperature of 25° C. Seeds are held under these conditions for 24 hours by which time the seeds reach a moisture content of 10% by weight. Seeds are then transferred to an open container at 40% relative humidity, 20° C. Moisture content is determined at 5% after 24 hours.

iii) Slow drying

Seeds are placed on petri dishes in a closed container (0.1 dm$^3$) containing a saturated solution of NaCl, at a drying temperature of 25° C. Moisture content above the saturated NaCl solution balances out at a relative humidity of 75% at 25° C. Seeds are held under these conditions for 72 hours by which time the seeds reach their final moisture content of 10%. Seeds are then transferred to an open container at 40% relative humidity, 20° C. Moisture content is determined at 5% after 24 hours.

Results are shown below in Table 3.

EXAMPLE 4

Shelf-life of Pregerminated Impatiens seeds 20 g seeds of Impatiens (cv Impulse red, Zaadunie BY), (lot 1) and 20 g seeds of Impatiens (cv Impulse scarlet, Zaadunie BY), (lot 2) are germinated for 4 days in aerated columns in 2 l of water at 20° C. 20 g germinated seeds having protruding radicles are obtained. Germinated seeds are selected, and centrifuged (1300 rpm / 1 min) to remove excess water and incubated for 7 days in a closed container at 8° C. to induce desiccation tolerance in the emerged radicle. Seeds have a moisture content determined at 47% by weight. The seeds are dried in still air, at a relative humidity of 40% and temperature of 20° C. After 48 hours the moisture content of the seeds is determined using the formula hereinbefore described, at 5% by weight. Dried seeds are divided up into 0.5 g portions which are sealed in aluminium-lined bags. Half of the bags of each seed lot are stored in a cooler at 8° C., the other half in a controlled environment chamber (Van den Berg, Montfoort, NL) at 20° C. Each month a bag is opened and 100 seeds are germinated on moistened filter paper at 25° C. in the light. The number of seeds forming secondary roots after 14 days incubation is counted. Control seed samples undergo pregermination however a drying step is not included in their treatment. Controls are stored at 8° C. and 20° C. Results are shown in Table 4.

EXAMPLE 5

A comparison of shelf lives of germinated Impatiens seeds having desiccation tolerant emerged radicles (moisture content of 5.0% by weight of seed) and germinated Impatiens seeds not having desiccation tolerant emerged radicles (moisture content of 19.6% by weight of seed).

40 g of Impatiens (cv Blitz salmon, Zaadunie BY) are germinated for 4 days in a column in 4 l of aerated water at 20° C. 20 g seeds (approx. 20,000 seeds) having emerged radicles are selected. One half of the seeds are dried immediately by first centrifuging at 1300 rpm for 2 minutes and then placing them in a plastic box in a fytotron conditioned at 25° C. and 80% RH. After 8 hours the moisture content of the seeds decreases from an initial 48% by weight to 19.6% by weight. Seeds are then divided into equal portions and placed in aluminium lined bags which are sealed and stored at three temperatures: −20° C., 8° C. and 20° C. The other half of the seeds after centrifuging, is incubated in air at 100% relative humidity in a closed container at 8° C. for 7 days, for the induction of desiccation tolerance in the radicle. Moisture content at the end of incubation is determined at 46% by weight. After incubation, seeds are dried at 25° C. and 80% RH. 24 hours after the start of drying, seeds are transferred to still air at 40% RH and 20° C., until the final moisture content of the seeds is determined at 5% by weight. Seeds are then divided into equal portions and packed in sealed bags (100 seeds/bag) and stored at −20° C., 8° C. and 20° C.

Immediately after drying and after suitable time intervals in storage, 100 seeds are incubated on moistened blotting paper at 25° C. The percentage of seedlings having developed secondary roots is determined 14 days after the start of incubation. Seeds are also tested for seedling emergence in a soil germination test i.e. 100 seeds are sown in soil at 20° C. and placed under fluorescent light. The percentage of seedlings is determined 14 days after sowing. Results are shown in Tables 5a and 5b.

EXAMPLE 6

A comparison of shelf lives of germinated tomato seeds with desiccation tolerant emerged radicles at 5% moisture content and seeds not having desiccation tolerant emerged radicles, 21.6% moisture content.

50 g of tomato seeds (F 7263, experimental variety, Zaadunie BV) are germinated in a column in 4 l of aerated water at 20° C. 4000 germinated seeds are selected after 3 days. One half of the germinated seeds are dried immediately by placing them in still air at 75% RH and 20° C. and permitted to reach a moisture content of 21.6% by weight. Initial moisture content of the seeds decreases from 50.6% by weight to 21.6% by weight in 6 hours. The other half of the seeds is transferred to a column with an aerated solution of PEG-8000, from BP Chemicals, (324 g/l),. Seeds remain in this solution for 7 days at a temperature of 8° C. in order to induce desiccation tolerance in the radicle. The seeds are then removed, rinsed in distilled water, and moisture content determined at 46%. Seeds are then dried in still air at 40% RH and 20° C. for 3 days. Seed moisture content is then determined to be 5%. Dried seeds of the two treatments (18×100 seeds) are then packed separately in aluminium lined bags which are sealed and stored at three temperatures: −20° C., 8° C. and 20° C. After predetermined storage periods, the quality of the seeds is tested by sowing 100 seeds per treatment on soil. Seeds are sown in trays on soil and placed for three days in the dark at 20° C. before removal to a greenhouse. Percentage of seedlings is determined two weeks after sowing.

Results in Table 6 show that shelf-life of seeds subjected to a desiccation tolerance induction treatment is longer at all storage conditions tested than for seeds which are directly dried back to a moisture content of 21.6%, and not subjected to a desiccation tolerance induction treatment.

EXAMPLE 7

A comparison of shelf lives of germinated Brussels sprouts seeds which have desiccation tolerant emerged radicles (5% moisture content), and non-desiccation tolerant seeds having emerged radicles (20% moisture content).

100 g of seeds of Brussels sprouts (cv. Tardis, Zaadunie BV) are germinated in 4 l aerated water at 23° C. After 16 hours germinated seeds are hand selected. 2100 seeds are selected. Moisture content of germinated seeds is determined at 50% by weight. 1000 seeds are incubated on blotting paper moistened with PEG-8000 (BP Chemicals ) solution (324 g/l, water potential −1.5 MPa, determined as per example 1), at a temperature of 8° C. for 7 days to induce desiccation tolerance in the emerged radicle. Moisture content is determined at 41% by weight at the end of the induction period. Seeds are rinsed in distilled water and placed in still air at 40% RH and 20° C. until a moisture content of 5% is reached after approximately 24 hours. The other 1000 seeds are dried immediately after hand selection in still air at 75% RH and 20° C. until a moisture content of 20.9% is reached after a period of 6 hours. Seeds are then sealed in aluminium lined bags (50 seeds per bag). Packaged seeds are stored at temperatures of −20° C., 8° C. and 20° C. After storage periods of 0, 1 and 2 months 50 seeds per treatment are sown on soil and the percentage of seedlings counted after 10 days. Results are shown in Table 7.

EXAMPLE 8

Seeds of Impatiens, cv Impulse salmon orange, having desiccation tolerant emerged radicles and performance on sowing simulator machines.

50 g of Impatiens, cv Impulse salmon orange are germinated in a column in 4 l of aerated water at a temperature of 20° C. After 3 days 30 g of seeds (approx. 30,000 seeds) with emerged radicles are selected.

15 g of seed (control) are placed on a sowing simulator. The other 15 g (test) are incubated in air in a closed container at 100% RH for 7 days at 8° C. so as to induce desiccation tolerance in the radicle. Moisture content of the seeds at the end of the induction step is determined at 44.3% by weight. After the induction step, the seeds are sown on a sowing simulator as described below.

A simulation of sowing is made on control and test samples by spreading seeds out in a layer on the bottom of a plastic tray and placing it in a fytotron (commercially available from Van den Berg, Montfoort, NL), conditioned at 20° C. and 40% relative humidity. The box is shaken regularly in order to simulate the vibration in the reservoir of a sowing machine. At regular intervals a sample of seeds is taken out of the tray. 1 g of the sample is used for moisture determination, and 2×50 seeds are sown in soil at 20° C. Emergence of the seeds is checked after 14 days.

Table 8 shows the advantage of having induced desiccation tolerance in the emerged radicle of pregerminated seeds over pregerminated seeds not having desiccation tolerant emerged radicles.

EXAMPLE 9

Comparison between Tomato seeds having desiccation tolerant emerged radicles and tomato seeds dried under conventional methods.

50 g tomato seeds (F 7263, experimental variety of Zaadunie BY) are germinated in a column in 4 l of aerated water at 20° C. After three days germinated seeds are selected and grouped as follows:

Group 1: Control. 500 seeds are placed in still air at a relative humidity of 40% and at a temperature of 20° C. for 7 days. Moisture content of the seeds is determined after 1 day and 7 days to be 6% by weight, respectively. Group 2: Direct drying to 20% by weight for moisture comparison test against seeds of the invention.

500 seeds are placed in still air at a relative humidity of 40% and at a temperature of 20° C. and removed when the moisture content reaches 20% by weight, after 6 hrs. The seeds are then placed in a closed container for 7 days at a temperature of 8° C. After this period, seeds are subdivided into two portions. One portion is placed onto moistened blotting paper and permitted to imbibe water for 4 days at 25° C. The second portion of seeds is dried back in still air at a relative humidity of 40% and at a temperature of 20° C. to a moisture content of 6%. Group 3: Seeds of the invention.

500 seeds are placed in a petri dish on filter paper moistened in PEG-8000 (BP Chemicals) solution (324 g/l, at a water potential of −1.5 MPa determined as per example 1). The petri dish is placed in a refrigerator for 7 days at a temperature of 8° C. to induce desiccation tolerance in the seeds. At the end of the period moisture content of the seeds is determined at 43% by weight. After this period, the seeds are rinsed with distilled water, and seeds are subdivided into two portions. One portion is placed onto moistened blotting paper and permitted to imbibe water for 4 days at 25° C. The second portion is dried back in still air at a relative humidity of 40% and at a temperature of 20° C. to a moisture content of 6%.

Sugar content of embryos is determined using the method of example 1, on the portion of dried seeds from seed of groups 2 and 3 and on seeds of group 1 after placing them in water for 2 hours and excising 25 embryos per group.

All seed groups (2×100 seeds per group) are placed on moistened blotting paper and permitted to imbibe water for 4 days at 25° C. Regeneration of secondary roots is then determined by counting. Results are shown in Table 9.

Table 9 shows that seeds of groups 2 and 3 are viable before a drying treatment. After a drying treatment seed viability of seeds of group 2 is comparable to that of seeds of group 1 which are subjected also to a drying treatment, however, the viability of seeds of the invention, group 3, is higher. Seeds of group 3 are desiccation tolerant.

EXAMPLE 10

Induction of desiccation tolerance in germinated seeds of Cucumber, Viola, and Petunia.

Seeds of cucumber (cv Airaris), Viola (cv Aurora yellow) and Petunia (cv White Flash), all of Zaadunie BV, are incubated on moistened filter paper at 20° C. in petri dishes enclosed in a box. In all cases, 250 seeds from each species having protruding radicles are selected after 3 days. Seeds of controls are immediately dried in still air at a RH of 40% and temperature of 20° C. Seeds of the test samples are incubated on blotting paper moistened with a PEG-8000 solution (324 g/l, at −1.5 MPa, determined as per example 1) for 7 days at 8° C. in a petri-dish under similar conditions as described in example 9 to induce desiccation tolerance in the radicle. The seeds are then rinsed in distilled water. Moisture contents after the induction step for cucumber, viola, and petunia are determined at 46%, 44% and 41% by weight respectively. The test samples are then dried in still air at 40% RH and 20° C. for 24 hours. 50 dried seeds are incubated on blotting paper moistened with water, at an ambient temperature of 25° C., and the development of seedlings is assessed after 14 days.

The sucrose content in cucumber axis and in viola embryos is determined using standard procedures (Boehringer-Mannheim supra) before the start of, and at the end of the incubation period. Results are shown in Table 10.

Table 10 shows a marked increase in the percentage of seedlings obtained from germinated seeds subjected to a desiccation tolerance treatment.

EXAMPLE 11

Induction of desiccation tolerance in the radicle of Cyclamen.

20 g of Cyclamen (cv. Marion, Zaadunie BY) are germinated in a column in 4 l of aerated water in the dark at 18° C. After 7 days 500 seeds are selected at a stage where it is clear that the radicles enclosed in endosperm are protruded from the seed coat i.e. the endosperm bulges out of the seed coat but radicle protrusion from the endosperm is not apparent. Seeds at this stage are either directly dried in still air at 40% RH and 20° C. (controls) or seeds (tests) are first incubated before drying in a petri dish with blotting paper moistened with a PEG-8000 solution at water potential of −1.5 MPa for 7 days following a similar procedure to that of Group 3 seeds of example 9, in order to induce desiccation tolerance in the emerged radicle. Moisture content of seeds is determined at the end of the induction period at 42% by weight.

After drying, 100 seeds of control and 100 test seeds are germinated on soil in the dark at a temperature of 18° C. The percentage of seedlings is determined 3 weeks after sowing.

The results in Table 11 show that seedling development increases markedly when drying is preceded by an incubation period.

EXAMPLE 12

Induction of desiccation tolerance in pregerminated Capsicum seeds.

5 g of Capsicum seeds (cv Astrion, Zaadunie BV) are incubated in a 4 l column in aerated water at 20° C. for 5 days. Germinated seeds are selected by hand, and divided into three portions of 100 seeds each. One portion is placed on a petri dish and dried in still air at 40% Pa, and 20° C., to a final seed moisture content of 7%. A second portion is incubated in a petri-dish on filter paper soaked with a solution of PEG-8000 (324 g/l at −1.5 MPa) for 7 days to induce desiccation tolerance in the emerged radicle. Moisture content of the seeds is determined at 45% by weight. Seeds are then dried under the same conditions as the first portion. The third portion is incubated in a PEG-8000 solution of −1.5 MPa for 7 days, containing indole butyric acid (IBA) at a concentration of 10 µM, to induce desiccation tolerance in the emerged radicle. Moisture content of the seeds is determined at 45% by weight. The seeds are then dried under the same conditions as for portion 2.

The dry seeds are incubated on moistened filter paper in closed containers for 8 days at a temperature of 25° C., and the percentage of seeds showing regrowth of the primary root recorded after 3 days. The percentage of seeds having primary and/or secondary roots is recorded after 8 days. Results shown in Table 12 indicate that germinated Capsicum seeds subjected to a desiccation step, survive desiccation conditions and show regrowth of the primary root and/or secondary root formation. Viability of the root is enhanced after IBA addition.

EXAMPLE 13

Survival of primary roots and growth of secondary roots from the hypocotyl region in tomato depends on length of the radicle, induction of desiccation tolerance in the radicle.

10 g seeds of tomato (cv. Elena, Zaadunie BY) are incubated on top of moistened filter paper at 20° C. in the light for 2 days. Half of the seeds are further incubated on filter paper soaked in a solution of 136 µM Paclobutrazol, (a synthetic gibberellin biosynthesis inhibitor, commercially available from ICI Plc) at 25° C. The remaining seeds are further incubated on moistened filter paper at 25° C. in the light. 600 germinated seeds having emerged radicles are selected after 1 day of incubating at 25° C. A selection of 100 seeds having emerged radicles of 0.5–1.5 mm, and of 100 seeds having emerged radicles of 1.5–2.5 mm is made. Selected seeds are either immediately dried in still air at 20° C., 40% R.H. for 24 hours to a final seed moisture content of 6% (control), or subjected to a treatment on filter paper moistened with a PEG-8000 solution (324 g/l; –1.5 MPa) at 8° C. for 6 days to induce desiccation tolerance in the emerged radicle. Moisture content is determined at 46% by weight. Seeds are then dried in still air under the same conditions as for control seeds to the same final seed moisture content. After drying, seeds are sown on top of moistened filter paper in closed containers at 25° C., in the light. Survival of the primary root is determined visually after 3 days. Survival is defined as primary roots showing no visible damage and continued growth. Secondary root formation from an hypocotyl region is measured after 7 days.

Table 13 shows that many emerged radicles die upon desiccation, but damage is more severe when the radicles are longer in length at the time of selection. Table 11 further shows that induction of desiccation tolerance results in an increase in survival of primary roots and a stimulation of secondary root formation. Treatment with Paclobutrazol results in a still higher survival of primary roots.

EXAMPLE 14

Incubation of germinated Impatiens seeds in PEG results in increases in sucrose content in cotyledons and radicles (hypocotyls) and increased desiccation tolerance.

10 g of seeds of Impatiens (cv. Impulse orange, Zaadunie BY) are germinated in a column containing 4 l of aerated water at 20° C. After three days 1600 germinated seeds are selected. 400 seeds (controls) are dried immediately in still air of 20° C. and 40% RH, and moisture content determined at 5% by weight, after 24 hours. 3 batches of 400 seeds each are incubated on blotting paper moistened with a solution of PEG-8000 (324 g/l, water potential at –1.5 MPa) at 8° C., in separate closed boxes for incubation periods of 1, 2 or 5 days. After incubation, seeds are rinsed in distilled water and blotted dry. Samples of each treatment (tests and controls) then undergo a sucrose determination: for each test and control 25 cotyledon pairs and 100 radicles (hypocotyls) are assessed. Remaining seeds are dried to a moisture content of 5% following the same procedure as for controls. Desiccation tolerance of dried seeds is assessed by sowing 2×50 seeds from each test and control on top of paper in the light at a temperature of 25° C. The percentage of seeds which develop into seedlings is assessed 14 days after sowing.

Table 14 shows that during incubation the sucrose content in the radicles rises markedly as does sucrose in the cotyledons. Desiccation tolerance of germinated seeds rises in parallel with elevating sucrose content.

TABLE 1

Emergence before and after drying, sucrose content in Impatiens seeds, after different treatments.

| length of incubation treatment (d) | emergence before desiccation (moisture content 44%) | emergence after desiccation (moisture content 5%) | sucrose content before desiccation (% of dry weight) |
|---|---|---|---|
| 0 | 98 | 1 | 0.8 |
| 1 | 97 | 7 | 1.1 |
| 2 | 98 | 42 | 2.0 |
| 3 | 96 | 87 | 2.4 |
| 6 | 98 | 97 | 3.7 |

TABLE 2

| Induction Period (days) | Radicle Sucrose Content (% of dry weight) | Emergence at 5 days (%) |
|---|---|---|
| 0 | 1.56 | 60 |
| 1 | 2.02 | 71 |
| 4 | 3.34 | 98 |
| 6 | 3.68 | 99 |

TABLE 3

| Treatment | Drying Rate | Sucrose Content after Drying (%) | Emergence (%) |
|---|---|---|---|
| direct drying (no incubation) | slow | 4.52 | 96 |
| | medium | 2.96 | 30 |
| | fast | 1.32 | 1 |
| 5 days incubation (before drying) | slow | 5.08 | 98 |
| | medium | 4.92 | 95 |
| | fast | 4.76 | 96 |

TABLE 4

Number of pregerminated treated Impatiens seeds out of 100 which form secondary roots after 14 days of incubation at 25° C. on moistened filter paper.

| storage period (months) | stored at 8° C. | | | | stored at 20° C. | | | |
|---|---|---|---|---|---|---|---|---|
| | ctrl | lot 1 | lot 2 | ave. | ctrl | lot 1 | lot 2 | ave. |
| 0 | 99 | 98 | 98 | 98 | 98 | 98 | 98 | 98 |
| 1 | 98 | 99 | 100 | 99 | 0 | 98 | 98 | 98 |
| 2 | 75 | 100 | 100 | 100 | — | 98 | 97 | 97 |
| 3 | 20 | 95 | 99 | 97 | — | 94 | 85 | 84 |
| 4 | 0 | 96 | 94 | 95 | — | — | — | — |
| 5 | — | 100 | 97 | 98 | | | | |
| 6 | — | 99 | 97 | 98 | | | | |
| 7 | — | 96 | 90 | 93 | | | | |

— = not attempted

TABLE 5a

Germination test on paper for seeds stored at 5 or 19.6% moisture content

| storage period | % seedlings with sec roots. Seeds stored at 5% moisture content | | | % seedlings with sec roots Seeds stored at 19.6% moisture content | | |
|---|---|---|---|---|---|---|
| (weeks) | −20° C. | 8° C. | 20° C. | −20° C. | 8° C. | 20° C. |
| 0 | — | 99 | — | — | 99 | — |
| 4 | 99 | 100 | 100 | 1 | 0 | 0 |
| 7 | 98 | 100 | 98 | 0 | 0 | 0 |
| 9 | 98 | 100 | 99 | 0 | 0 | 0 |
| 13 | 98 | 98 | 98 | — | — | — |
| 18 | 100 | 99 | 99 | — | — | — |
| 24 | 92 | 98 | 90 | — | — | — |

TABLE 5b

Germination test on soil for seeds stored at 5% or 19.6% moisture content at different temperatures

| storage period | % seedlings (5% moisture content) | | | % seedlings (19.6% moisture content) | | |
|---|---|---|---|---|---|---|
| (weeks) | −20° C. | 8° C. | 20° C. | −20° C. | 8° C. | 20° C. |
| 0 | — | 97 | — | — | 96 | — |
| 5 | 95 | 93 | 95 | 0 | 0 | 0 |
| 7 | 98 | 97 | 97 | — | — | — |
| 9 | 97 | 95 | 96 | — | — | — |
| 13 | 94 | 96 | 91 | — | — | — |
| 18 | 93 | 94 | 85 | — | — | — |
| 24 | 92 | 88 | 73 | 0 | 0 | 0 |

TABLE 6

| storage period | % seedlings for seeds stored at 5% moisture content | | | % seedlings for seeds stored at 21.6% moisture content | | |
|---|---|---|---|---|---|---|
| (weeks) | −20° C. | 8° C. | 20° C. | −20° C. | 8° C. | 20° C. |
| 0 | — | 90 | — | — | 89 | — |
| 2 | — | 90 | — | — | 49 | — |
| 8 | 93 | 91 | 95 | 12 | 2 | 2 |
| 12 | 90 | 90 | 90 | 8 | 4 | 0 |
| 16 | 91 | 91 | 93 | 2 | 1 | 0 |
| 24 | 94 | 94 | 93 | — | — | — |

TABLE 7

Percentage of plants obtained after sowing treated Brussels sprouts seeds in soil.

| storage period | seeds at 20.9% seed moisture storage temperature (°C.) | | | seeds at 5% seed moisture storage temperature (°C.) | | |
|---|---|---|---|---|---|---|
| (months) | −20 | 8 | 20 | −20 | 8 | 20 |
| 0 | 94 | 94 | 94 | 92 | 92 | 92 |
| 1 | 34 | 78 | 2 | 94 | 90 | 86 |
| 2 | 20 | 74 | 0 | 94 | 94 | 90 |

TABLE 8

| Time on sowing simulator | Non-treated seeds | | Seeds with Des. tol. emerged radicles | |
|---|---|---|---|---|
| (mins) | % moisture | emergence | % moisture | emergence |
| 0 | 45.9 | 96 | 44.3 | 95 |
| 30 | 32.7 | 97 | 33.7 | 94 |
| 60 | 19.8 | 97 | 21.3 | 93 |
| 120 | 8.0 | 65 | 8.1 | 93 |
| 180 | 6.1 | 63 | 6.5 | 93 |
| 240 | 6.7 | 50 | 5.7 | 91 |

TABLE 9

| treatment | % of seeds showing root elongation 7 days/8° C./4 days water imbibition (no drying) | % of seeds showing secondary root formation 7 days/8° C./4 days water imbibition. (with drying) | sucrose content (µg/embryo) |
|---|---|---|---|
| Group 1 | — | 70 | 38.6 |
| Group 2 | 98 | 76 | 38.4 |
| Group 3 | 100 | 100 | 52.6 |

TABLE 10

| species | % seedlings Untreated | % seedlings Treated | % Sucrose Before | % Sucrose After |
|---|---|---|---|---|
| cucumber | 8 | 100 | 3.17 | 10.55 |
| viola | 33 | 94 | 3.70 | 6.34 |
| petunia | 8 | 93 | — | not determined |

TABLE 11

| treatment | % seedlings | % non-emerged seeds |
|---|---|---|
| Control | 23 | 77 |
| Test | 94 | 6 |

TABLE 12

| Treatment | % seeds with regrowth of primary root after 3 days | % seeds with primary and/or secondary roots after 8 days |
|---|---|---|
| Portion 1 (Control) | 10 | 86 |
| Portion 2 | 54 | 90 |
| Portion 3 | 72 | 96 |

TABLE 13

| | Length of emerged radicle | | | |
| --- | --- | --- | --- | --- |
| | 0.5–1.5 mm | | 1.5–2.5 mm | |
| | Primary root survival (3 days) | Secondary root formation from hypocotyl region (7 days) | Primary root survival (3 days) | Secondary root formation from hypocotyl region (7 days) |
| Control | 37 | 85 | 0 | 64 |
| PEG | 97 | 100 | 37 | 100 |
| Paclobutrazol plus PEG | 97 | 100 | 83 | 100 |

TABLE 14

| | Percentage of seeds developing into seedlings 14 days after sowing. | | |
| --- | --- | --- | --- |
| | (% of dry weight) | | |
| treatment | hypocotyl sucrose content | cotyledon sucrose content | % seedlings |
| control | 0.70 | 0.57 | 2 |
| 1d PEG | 4.23 | 1.93 | 68 |
| 2d PEG | 4.82 | 2.15 | 75 |
| 5d PEG | 7.40 | 2.74 | 96 |

We claim:

1. Pregerminated seeds comprising desiccation tolerant emerged radicles wherein the emerged radicles contain elevated levels of sucrose relative to non-desiccation tolerant emerged radicles of the same plant species and wherein said desiccation tolerant seeds have an overall moisture content in the range of about 35% to about 55% by weight of the seeds and are capable of resuming growth when planted.

2. Pregerminated seeds according to claim 1 wherein said seeds have been stored at ambient storage conditions.

3. Pregerminated seeds comprising desiccation tolerant emerged radicles wherein the emerged radicles contain elevated levels of sucrose relative to non-desiccation tolerant emerged radicles of the same plant species and the moisture content of said desiccation tolerant seeds lies in the range of about 4% to about 12% by weight of the seeds and are capable of resuming growth when planted.

4. Pregerminated seeds according to claim 1 wherein the seeds are selected from plants of the group consisting of Alliums, Antirrhinums, Begonias, Brassicaceae, Capsicums, Cucurbitaceae, Lycopersicons, Cyclamens, Betas, Dianthuses, Gazanias, Gerberas, Impatiens, Lobelias, Nicotianas, Pelargoniums, Petunias, Phloxes, Primulas, Raphanuses, Salvias, Solanums, Tagetes, Verbenas, Vincas, Violas, Apiums, Chicoriums, Daucuses and Zinnias.

5. Pregerminated seeds according to claim 1 further comprising a seed coating.

6. Pregerminated seeds according to claim 1 wherein the desiccation tolerance is located in the hypocotyl region of the radicle.

7. Pregerminated seeds according to claim 3 wherein the seeds are selected from the group consisting of, Allium, Antirrhinums, Begonias, Brassicaceeae, Capsicums, Cucurbitaceae, Lycopersicons, Cyclamens, Betas, Dianthuses, Gazanias, Gerberas, Impatiens, Lobelias, Nicotianas, Pelargoniums, Petunias, Phloxes, Primulas, Raphanuses. Salvias, Solanums, Tagetas, Verbenas, Vincas, Apiums, Chicoriums, Daucuses, and Violas.

8. Pregerminated seeds according to claim 3 further comprising a seed coating.

9. Pregerminated seeds according to claim 3 wherein the seeds are Impatiens seeds.

10. Pregerminated seeds according to claim 3 wherein the seeds are Pansy seeds.

11. Pregerminated seeds comprising desiccation tolerant emerged radicles and having an overall moisture content in the range of about 35% to about 55% by weight of the seed wherein the embryos of the seed have an elevated sucrose level relative to the embryos of pregerminated seeds with non-desiccation tolerant emerged radicles of the same plant species.

12. Pregerminated seeds comprising desiccation tolerant emerged radicles wherein the moisture content of said seeds is in the range of about 4% to about 12% wherein the embryos of the desiccation tolerant seeds have an elevated sucrose level relative to the embryos of pregerminated seeds with non-desiccation tolerant emerged radicles of the same plant species.

13. Pregerminated seeds according to claim 11 wherein the seeds are salaried from the group of seeds consisting of Impatiens, Viola, Pansy and Cyclamen.

14. Pregerminated seeds according to claim 12 wherein the seeds are selected from the group of seeds consisting of Impatiens, Viola, Pansy and Cyclamen.

15. Pregerminated seeds according to claim 1 wherein the seeds are Impatiens seeds.

16. Pregerminated seeds according to claim 3 wherein said seeds have been stored at ambient storage conditions.

17. Pregerminated seeds according to claim 3 wherein the desiccation tolerance is located in the hypocotyl region of the radicle.

* * * * *